US005531675A

United States Patent [19]

Yoo

[11] Patent Number: 5,531,675

[45] Date of Patent: Jul. 2, 1996

[54] MICRO-ACUPUNCTURE NEEDLE FOR A FINGER OF A HAND

[76] Inventor: Tae W. Yoo, 807 1-Dong, Hanyang Apt., San 189-1, Seocho-dong Seocho-Ku, Seoul, Rep. of Korea

[21] Appl. No.: 882,352

[22] Filed: May 6, 1992

Related U.S. Application Data

[63] Continuation of Ser. No. 388,700, Aug. 2, 1989, abandoned.

[30] Foreign Application Priority Data

May 10, 1989 [KR] Rep. of Korea ................. 19896089 U

[51] Int. Cl.$^{6}$ ................................ A61M 1/30

[52] U.S. Cl. ................................ 604/20; 606/189

[58] Field of Search ................................ 128/744; 606/907, 606/189, 204; 604/20, 46, 48, 51

[56] References Cited

U.S. PATENT DOCUMENTS

| | | | |
|---|---|---|---|
| 3,136,314 | 8/1960 | Kravitz | 604/46 |
| 3,923,064 | 12/1975 | Leupold | 606/189 |
| 4,549,536 | 10/1985 | Varjabedian | 606/189 |

FOREIGN PATENT DOCUMENTS

| | | | |
|---|---|---|---|
| 0082081 | 6/1983 | European Pat. Off. | 606/189 |
| 0197831 | 10/1986 | European Pat. Off. | 606/189 |

*Primary Examiner*—C. Fred Rosenbaum
*Assistant Examiner*—V. Alexander
*Attorney, Agent, or Firm*—Felfe & Lynch

[57] ABSTRACT

A micro-acupuncture needle for a finger of a hand comprises a sharp needle of a substantially cone-shaped protuberance made by molding a metal sheet of at least one of a group of aluminum and copper.

2 Claims, 1 Drawing Sheet

MICRO-ACUPUNCTURE NEEDLE FOR A FINGER OF A HAND

This application is a continuation of application Ser. No. 388,700, filed Aug. 2, 1989, now abandoned.

The present invention relates to a micro-acupuncture needle for use on a finger of a hand, which causes finger compression effects, pricking the acupuncture needle into the blood vessel section of a human finger, as well as providing effects of ionized reactions, which are generated from the metal of the device, smeared or conducted into the blood stream in the finger.

The micro-acupuncture needle comprises a needle bar and a piece of adhesive tape which provides a fixing force for the needle to settle, and the micro needle (acupuncture) of a conventional device and method is used for those cases of an acupuncture treatment which require a rather longer period of care.

The present invention uses a method and components which are very much different from the conventional finger acupuncturing and compressing method. In accordance with the invention, a protuberance, which is molded in a sharply projected shape, is compressed onto the diseased area and/or the blood vessel area, that provide the finger compression (impacting) effect. Ionizing effects which are generated from an aluminum or copper plate, which is formed for the protuberance base, causes acceleration of blood circulation.

In accordance with the invention, a micro-acupuncture needle comprises a sharp needle edge of a substantially cone-shaped protuberance made by molding a metal sheet of at least one of the group of aluminum and copper.

For a better understanding of the invention, together with other and further objects thereof, reference is made to the following description, taken in connection with the accompanying drawing, and its scope will be pointed out in the appended claims.

Referring now to the drawing.

Figure 1:
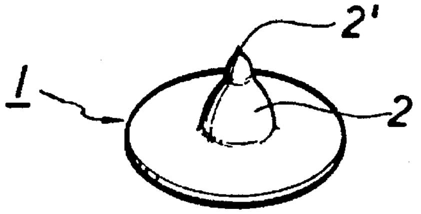
FIG. 1 is a perspective view of a micro-acupuncture needle for a finger of a hand in accordance with the invention.
Figure 2:
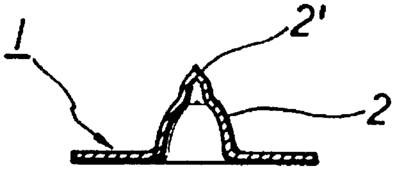
FIG. 2 is an elevational view, taken in section, of the FIG. 1 needle.

Referring now to FIG. 1, a protuberance is formed by molding one side of a metal sheet substantially into a cone shape, an end section 2' of which is formed with a needle sharpness. Aluminum or copper sheet preferably is used for the metal sheet.

Referring to FIGS. 1–4, the aforementioned device is used in such a way that the sharply shaped protuberance end 2 and its base plate 1 is closely contacted with human body surface, and the needle edge and the base plate of the protuberance is adherently fixed onto the skin, preferably by means of applying an appropriate size of adhesive tape 3, which provides the following described reaction and effects.

When the metal sheet is closely adhered on the selected spot of blood vessel or nerve system circuit, the sharply shaped edge section 2' of the protuberance 2 is firmly pressed down and the adhesive tape 3 is adherently applied to cover and fix the protuberance position. The sharply shaped edge section imposes strong compression forces on the skin and the blood vessel, which create an accurate and sound finger compression effect.

As the human skin surface is firmly adhered with the needle shaped edge section 2' of the protuberance 2, the negative (–) ions, being generated from the material reaction of the metal sheet 1, are induced into the blood flowing through the blood vessel of the human body, which are accessed toward the positive (+) ions being existed in the blood in the blood vessel, causing the positive (+) ions to be reacted and widely and rapidly dispersed.

Therefore, all the refuses in the blood vessel carrying the positive (+) ions, are penetrated and attracted by the negative (–) ions, causing the refuses in the blood stream to be dispersed. Eventually, the refuses are dispersed and reduced and blood circulation becomes more vitalized.

Figure 3:
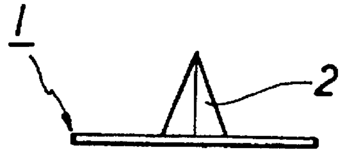
FIG. 3 is an elevational view of a modified micro-acupuncture needle in accordance with the invention.
Figure 4:
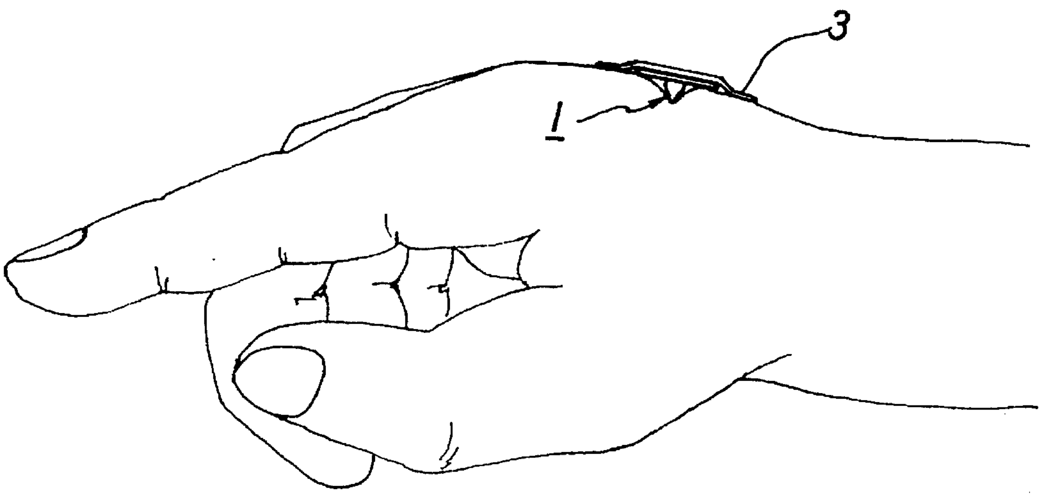
FIG. 4 is a side view of the FIG. 1 needle, to a reduced scale, on a hand.

In the case when the protuberance 2 with a triangular shaped acupuncture needle of FIG. 3 is applied, the same reaction effects occur as the conditions above described.

The present invention is easy to use and apply, and the results from the treatment are conspicuous and beneficial, thus eliminating the pains from the treated zone/section of the body.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1.A micro-acupressure needle comprising a sharp needle edge of a substantially cone-shaped sole protuberance which has a rounded lower portion and a rounded upper portion which peaks in said sharp needle edge, said rounded lower portion being constricted inwardly at a region thereof contiguous with said rounded upper portion and which protuberance is a portion of and extends from a metal sheet formed from one or more materials selected from the group consisting of aluminum and copper.

2. A needle in accordance with claim 1 in which said metal sheet is attached to and backed by adhesive tape extending beyond said metal sheet for attaching the needle to a hand.

* * * * *